US010982246B2

(12) United States Patent
Pérez Cruz et al.

(10) Patent No.: US 10,982,246 B2
(45) Date of Patent: Apr. 20, 2021

(54) METHOD FOR OBTAINING 1-KESTOSE

(71) Applicant: Centro de Ingenierla Genética y Biotecnologia, Havana (CU)

(72) Inventors: Enrique Rosendo Pérez Cruz, Sancti Spíritus (CU); Lázaro Hernández Garcia, Havana (CU); Duniesky Martínez García, Sancti Spíritus (CU); Luis Enrique Trujillo Toledo, Havana (CU); Carmen Menéndez Rodríguez, Havana (CU); Alina Sobrino Legón, Sancti Spíritus (CU); Ricardo Ramírez Ibañez, Havana (CU); Gumersindo Feijoo Costa, Ames (ES); Juan Manuel Lema Rodicio, Teo (ES)

(73) Assignee: Centro de Ingenierla Genética y Biotecnologia, Havana (CU)

( * ) Notice: Subject to any disclaimer, the term of this patent is extended or adjusted under 35 U.S.C. 154(b) by 0 days.

(21) Appl. No.: 16/166,215

(22) Filed: Oct. 22, 2018

(65) Prior Publication Data

US 2019/0085364 A1   Mar. 21, 2019

Related U.S. Application Data

(62) Division of application No. 14/428,534, filed as application No. PCT/CU2013/000005 on Sep. 18, 2013, now Pat. No. 10,131,927.

(30) Foreign Application Priority Data

Sep. 18, 2012 (CU) .................................. 2012/0138

(51) Int. Cl.
| | |
|---|---|
| *C12P 19/00* | (2006.01) |
| *A23L 5/00* | (2016.01) |
| *A23L 29/30* | (2016.01) |
| *A23L 27/30* | (2016.01) |
| *A23L 33/10* | (2016.01) |
| *A23L 2/60* | (2006.01) |
| *C12P 19/18* | (2006.01) |
| *C07H 3/00* | (2006.01) |
| *C07H 3/02* | (2006.01) |
| *A23K 20/163* | (2016.01) |
| *C07H 3/06* | (2006.01) |
| *C12N 9/10* | (2006.01) |

(52) U.S. Cl.
CPC ............ *C12P 19/00* (2013.01); *A23K 20/163* (2016.05); *A23L 2/60* (2013.01); *A23L 5/00* (2016.08); *A23L 27/33* (2016.08); *A23L 29/30* (2016.08); *A23L 33/10* (2016.08); *C07H 3/00* (2013.01); *C07H 3/02* (2013.01); *C07H 3/06* (2013.01); *C12N 9/1051* (2013.01); *C12P 19/18* (2013.01); *C12Y 204/01099* (2013.01)

(58) Field of Classification Search
None
See application file for complete search history.

(56) References Cited

U.S. PATENT DOCUMENTS

| | | | |
|---|---|---|---|
| 4,309,505 A | 1/1982 | Smith et al. | |
| 4,797,360 A | 1/1989 | Doelle | |
| 4,849,356 A | 7/1989 | Van Dooren et al. | |
| 4,927,757 A | 5/1990 | Hatcher et al. | |
| 5,463,038 A | 10/1995 | Hidano et al. | |
| 6,479,657 B1 | 11/2002 | Nishizawa et al. | |
| 7,655,449 B2 | 2/2010 | Nakamura et al. | |

FOREIGN PATENT DOCUMENTS

| | | |
|---|---|---|
| BR | PI0705359 A2 | 12/2009 |
| EP | 0663442 A1 | 7/1995 |
| JP | 2010273580 A | 12/2010 |
| WO | WO9601904 | 1/1996 |
| WO | WO2005051102 A1 | 6/2005 |
| WO | WO2010103150 A1 | 9/2010 |

OTHER PUBLICATIONS

Rehm et al., "Production of 1-Kestose in Transgenic Yeast Expressing a Fructosyltransferase from Aspergillus foetidus," Journal of Bacteriology, vol. 180, No. 5, pp. 1305-1310, Mar. 1998.
Luscher et al., "Cloning and Functional Analysis of Sucrose:Sucrose 1-Fructosyltransferase from Tall Fescue," Plant Physiology, vol. 124, pp. 1217-1227, Nov. 2000.
Nishizawa et al., "Kinetic Study on Transfructosylation by B-Fructofuranosidase from Aspergillus niger ATCC 20611 and Availability of a Membrane Reactor for Fructooligosaccharide Production," Food Sci. Technol. Res., vol. 7 (1), pp. 39-44, 2001.

(Continued)

*Primary Examiner* — Iqbal H Chowdhury
(74) *Attorney, Agent, or Firm* — Hoffmann & Baron, LLP

(57) ABSTRACT

The present invention discloses an industrial scale method to obtain 1-kestose by the use of a recombinant fructosyltransferase (FTF), isolated from *Festuca arundinacea*, expressed constitutively in a non-saccharolytic yeast. In this invention, the recombinant FTF type sucrose:sucrose 1-fructosyltransferase (1-SSTrec) is produced constitutively, stable and at high yield, both in the culture supernatant and in intact cells of the host *Pichia pastoris*. Hence, the invention additionally provides a method for 1-SST production at industrial scale. The recombinant enzyme is then used for mass production of short-chain fructooligosaccharides (FOS), specifically 1-kestose, from sucrose. The method of the present invention establishes conditions that allow conversion rates where the synthesized FOS constitute above 55% (w/w) of the total sugars in the reaction mixture and the 1-kestose content reaches values higher than 90% (w/w) of the total FOS fraction.

9 Claims, 4 Drawing Sheets

(56) References Cited

OTHER PUBLICATIONS

A. Franck, "Technological functionality of inulin and oligofructose," British Journal of Nutrition, vol. 87, Suppl. 2, pp. S287-S291, 2002.
Altenbach et al., "The large subunit determines catalytic specificity of barley sucrose:fructan 6-fructosyltransferase and fescue sucrose:sucrose 1-fructosyltransferase," FEBS Letters vol. 567, 28431, pp. 214-218, 2004.
Hidaka et al., "A Fructooligosaccharide-producing Enzyme from Aspergillus niger ATCC 20611," Agric. Biol. Chem., vol. 52, 5, pp. 1181-1187, 1988.
Ohtsuka et al., "Characterization of Levansucrase from Rahnella aquatilis JCM-1683," Bioscience, Biotechnology, and Biochemistry, vol. 56:9, pp. 1373-1377, 2014.
Gibson et al., "Dietary Modulation of the Human Colonic Microbiota:Introducing the Concept of Prebiotics," The Journal of Nutrition, vol. 125 (6), pp. 1401-1412, 1995.
Hochstrasser et al., "Expression of a functional barley sucrose-fructan 6-fructosyltransferase in the methylotrophic yeast *Pichia pastoris*," Federation of European Biochemical Societies,FEBS Letters, FEBS 21238, vol. 440, pp. 356-360, 1998.
Avila-Fernandez et al., "Molecular characterization of sucrose:sucrose 1-fructosyltransferase (1-SST) from *Agave tequilana* Weber var. *azul*.," Science Direct-Plant Science, vol. 173, pp. 478-486, 2007.
Sanchez et al., "Fructooligosaccharides production by *Aspergillus* sp. N74 in a mechanically agitated airlift reactor," Science Direct—Food and Bioproducts Processing, vol. 86, pp. 109-115, 2008.
Trujillo et al., "Constitutive expression of enzymatically active Gluconacetobacter diazotrophicus levansucrase in the methylothrophic yeast *Pichia pastoris*," AFINIDAD (Affinity), vol. 59 (500), pp. 365-370, 2002.
Cuenca-Estrella et al., "*Scopulariopsis brevicaulis*, a Fungal Pathogen Resistant to Broad-Spectrum Antifungal Agents," Antimicrobial Agents and Chemotherapy, vol. 47, No. 7, pp. 2339-2341, 2003.
Driouch et al., "Optimized bioprocess for production of fructofuranosidase by recombinant Aspergillus niger," Appl Microbiol Biotechnol, vol. 87, pp. 2011-2024, 2010.
Ahmad et al., "Nonlinear process modeling of fructosyltransferase (FTase) using bootstrap re-sampling neural network model," Bioprocess Biosyst Eng, vol. 33, pp. 599-606, 2010.
Vega et al., "Enzymatic synthesis of fructooligosaccharides with high 1-kestose concentrations using response surface methodology," Bioresource Technology, vol. 102 (22), pp. 10180-10186, 2011.
Vankova et al., "Design and economics of industrial production of fructooligosaccharides," Chemical Papers, vol. 62(4), pp. 375-381, 2008.
Dorta et al., "Sugarcane molasses and yeast powder used in the Fructooligosaccharides production by Aspergillus iaponicus-FCL 119T and Aspergillus niger ATCC 20611," Journal of Industrial Microbiology and Biotechnology, vol. 33, pp. 1003-1009, 2006.
Ghazi et al., "Immobilisation of fructosyltransferase from Aspergillus aculeatus on epoxy-activated Sepabeads EC for the synthesis of fructo-oligosaccharides," Journal of Molecular Catalysis B: Enzymatic, vol. 35, pp. 19-27, 2005.
Hang et al., "Production of Kestose from Molasses with Commercial Juice Processing Enzyme Preparation Containing Fructosyitransferase," Biotechnology Letters, vol. 17, No. 11, pp. 1167-1168, 1995.
Lasseur et al., "Molecular and functional characterization of a cDNA encoding fructan:fructan 6G-fructosyltransferase (6G-FFT)/fructan:fructan 1-fructosyltransferase (1-FFT) from perennial ryegrass (*Lolium perenne* L.)," Journal of Experimental Botany, vol. 57, No. 11, pp. 2719-2734, 2006.
Mussatto et al., "Fructooligosaccharides and B-fructofuranosidase production by Aspergillus japonicus immobilized on lignocellulosic materials," Journal of Molecular Catalysis B; Enzymatic 59, pp. 76-81, 2009.
Schroeven et al., "Transforming wheat vacuolar invertase into a high affinity sucrose:sucrose 1-fructosyltransferase," New Phytologist 180, pp. 822-831, 2008.
Vijn et al., "Cloning of Sucrose:Sucrose 1-Fructosyltransferase from Onion and Synthesis of Structurally Defined Fructan Molecules from Sucrose," Plant Physiology 117, pp. 1507-1513, 1998.
Guio et al., "Recent Trends in Fructooligosaccharides Production," Recent Patents on Food, Nutrition & Agriculture, vol. 1, No. 3, 2009.
Vega-Paulino et al., "Potential application of commercial enzyme preparations for industrial production of short-chain fructooligosaccharides," Journal of Molecular Catalysis B: Enzymatic vol. 76, pp. 44-51, 2012.
Andreoletti et al., "The maintenance of the list of QPS microorganisms intentionally added to food or feed, Scientific Opinion of the Panel on Biological Hazards, (Question No. EFSA-Q-2008-006)," The EFSA Journal vol. 923, pp. 1-48, 2008.
Van Der Meer, et al., "Cloning of the fructan biosynthesis pathway of Jerusalem artichoke," The Plant Journal vol. 15 (4), pp. 489-500, 1998.
Judd, S., "The status of membrane bioreactor technology," Trends in Biotechnology 25 (2); pp. 109-116, 2008.
Yun, J., "Fructooligosaccharides-Occurrence, preparation, and application," Enzyme and Microbial Technology 19, pp. 107-117, 1996.
Kawakami, et al., "Molecular Characterization of Sucrose:Sucrose 1-Fructosyltransferase and Sucrose:Fructan 6-Fructosyltransferase Associated with Fructan Accumulation in Winter Wheat during Cold Hardening," Biosci, Biotechnol, Biochem., 66 (11), 2297-2305, 2002.
Romanos, et al., "Pichia Protocols, The Generation of multicopy recombinant strains," vol. 103, pp. 55-72, 1998, Edited by David Higgins and James Cregg (Book).
Cereghino, et al., "Heterologous protein expression in the methylotrophic yeast *Pichia pastoris*," FEMS Microbiology Reviews 24 (2000) pp. 45-66.
Weyens, et al., "Production of tailor-made fructans in sugar beet by expression of onion fructosyltransferase genes," Plant Biotechnology Journal (2004), 2: 321-327.

METHOD FOR OBTAINING 1-KESTOSE

This application is a divisional of U.S. application Ser. No. 14/428,534, filed Mar. 17, 2015, which is a U.S. National Phase of, and Applicant claims priority from, International Patent Application No. PCT/CU2013/000005, filed Sep. 18, 2013, which claims priority from CU 2012/0138, filed Sep. 18, 2012, each of which is incorporated herein by reference in its entirety.

TECHNICAL FIELD

The present invention relates to the food and sugar industries, in particular to fructooligosaccharides (FOS) synthesis from cane/beet sugar or other sucrose-containing raw materials as honey, molasses, plant extracts, syrups, etc.

PRIOR ART

FOS are composed by linear chains with 1-9 fructose residues linked to a sucrose molecule by a β2→1 bond (Yun, 1996, Enzyme Microb. Technol. 19:107-117). The importance of these compounds lies in their use as indigestible ingredients of the diet, in humans and in animals, having a prebiotic effect, as they produce health benefits by selectively stimulating the growth or the activity of one or more types of friendly microorganisms in the colon. Among these microorganisms are species of the genera *Lactobacillus* and *Bifidobacterium* (Gibson and Roberfroid., 1995, J. Nutr. 125 (6): 1401-1412). In nature, FOS are produced in plants, fungi, bacteria and some yeasts by the action of enzymes so called fructosyltransferases (FTF, EC 2.4.1.9) and β-fructofuranosidases (EC 3.2.1.26) (Guío et al., 2009; Recent Patents on Food, Nutrition & Agriculture 1 (3): 221-30).

Industrial FOS production is currently performed following two strategies: —partial degradation of inulins (Yun., 1996; *Enzyme Microb. Technol.* 19:107-117; Franck., 2002; British Journal of Nutrition 87 (2): S287-S291), or enzymatic synthesis from sucrose, by using β-fructofuranosidase with high transfructosylase activity or FTF, produced mainly by fungi (*Aspergillus niger, A. japonicus, A. oryzae, A. aculeatus* and *Aureobasidium pullulans*) (Yun., 1996; *Enzyme Microb. Technol.* 19:107-117; Vaňková et al., 2008; *Chemical Papers* 62 (4) 375-381). Both technologies yield a mixture of FOS that has a variable degree of polymerization (DP) from 2 to 10, which main components are: 1-kestose ($GF_2$), nystose ($GF_3$), fructosylnystose ($GF_4$), bifurcose ($GF_3$) inulobiose ($F_2$), inulotriose ($F_3$) and inulotetraose ($F_4$). From the commercial point of view, the trisaccharide 1-kestose is the most valuable FOS due to its double importance as natural prebiotic and low calorie sweetener useful as sugar substitute for diabetic patients (Vega and Zuniga-Hansen., 2011; Bioresource Technology 102 (22), 10180-10186).

Technologies and patent documents regarding FOS production from sucrose are based on the use of cells and enzymes (either free or immobilized) isolated from different wild-type microorganisms such as the fungi *Aureobasidium pullulans* (Smith and Luenser, 1980. U.S. Pat. No. 4,309,505), *Aspergillus phoenicis* (Van Dooren et al., 1988. U.S. Pat. No. 4,849,356), *Aspergillus niger* (Hidaka et al., 1988, Agric. Biol Chem 1181), *Aspergillus aculeatus* (Fernandez-Arrojo et al., 2009. Patent Application WO 2010/103150 A1), the yeast *Rhodotorula* sp. (Agular de Oliveira et al., 2007. BRPI0705359 Patent Application A2-2), and the bacteria *Microbacterium laevaniformans* (Hatcher et al., 1988. U.S. Pat. No. 4,927,757), *Rahnella aquatilis* (Ohtsuka, K. et al. Biosci. Biotech. BioChem. 56 (9), 1373-1377, 1992), *Zymomonas mobilis* (Hatcher et al., 1988. U.S. Pat. No. 4,797,360). These production processes are carried out in different kind of reactors, mainly in stirred tanks and fixed bed, operating either discontinuously or continuously. In discontinuous processes, the accumulation of the released glucose may inhibit the FOS synthesis reaction. On the other hand, continuous processes using cells or enzymes immobilized on different supports allow reuse of the biocatalyst but cannot be operated at high flow rates due to internal diffusional restrictions for the substrate to access the immobilized enzyme. Reaction times need to be adjusted to avoid hydrolysis of the synthesized fructans. The incubation times are dependent on the initial amount of enzyme activity per gram of substrate varying from 8 to 24 hours, when a mixture of 1-kestose, nystose and fructosylnystose is synthesized.

The production of pure 1-kestose crystals or 1-kestose preparations with purity over 90% (Tetsuhiro et al., 1995. U.S. Pat. No. 5,463,038; Koichiro et al., 2010. Patent Application JP2010273580-A) is an extremely complex process when it starts from most common reaction mixtures composed of 20-25% glucose, 10-15% sucrose, 5% fructose, and 55-60% total FOS, and from the FOS with 40% to 60% 1-kestose. The process can be economically unviable for its use in foods. The chromatographic separation of 1-kestose is economically feasible only when its content represents above 80% of the total FOS fraction (Nishizawa et al., 1996. U.S. Pat. No. 6,479,657). Mixtures of reactions where the content of FOS is mainly 1-kestose (more than 80% of the sugars in the mixture) are infrequent. High levels of 1-kestose have been synthesized by FTF enzymes from fungi such as *Aspergillus aculeatus* (Hang and Woodams, 1995, Biotechnology Letters 17: 295-298) and *Aspergillus japonicus* ATCC 20236, at sucrose concentrations lower than 227 g/L (Mussatto et al., 2009, Journal of Molecular Catalysis B: Enzymatic 59: 76-81). In both reports, the 1-kestose content was about 71% of the total FOS fraction present in the mixture, but when sucrose concentrations were tested over 500 g/L the 1-kestose percentage decreased to values close or lower than 60% (Ghazi et al., 2005, Journal of Molecular Catalysis B: Enzymatic 35: 19-27). β-fructofuranosidases from *Aspergillus niger* ATCC 20611, *Penicillium roqueforti* and *Scopulariopsis brevicaulis* are able to produce 1-kestose up to 76.7%, 86.7% and 91.3%, respectively, at sucrose concentrations of 500 g/L (Nishizawa et al., 2002. U.S. Pat. No. 6,479,657 B1). Although these percentages show that the enzymes from *P. roqueforti* and *S. brevicaulis* are superior in regard to 1-kestose yield than those of *A. niger*, the situation changes in terms of productivity and stability. In addition, none of these organisms are recognized as safe (GRAS or QPS, General Recognized as Safe or Qualified Presumption of Safety) for use in food (EFSA Panel on Biological Hazards., 2009; EFSA Journal 7 (12): 1431; Cuenca-Estrella et al., 2003, Antimicrob Agents Chemother 47 (7): 2339-2341).

The growth of filamentous fungi is another huge productive limitation in industrial fermentations, since their filaments are wrapped to the propeller blades and also often block the fermentor air vents (Ahmad et al., 2010, Bioprocess Eng Biosyst 33, 599-606).

A mutated variant of the *A. niger* β-fructofuranosidase was created by protein engineering. The mutated gene was expressed in a β-fructofuranosidase-deficient strain of this same fungus. The enzyme synthesized 1-kestose to represent 93.5% of the total FOS when reacted with sucrose at a concentration of 550 g/L (Nakamura et al., 2010. U.S. Pat. No. 7,655,449).

However, there are no technologically viable FTF production systems that allow the availability of such enzymes in vast amounts for industrial FOS production (Vega and Zuniga-Hansen, 2011; Bioresource Technology 102 (22): 10180-10186). Fungi cultivation and subsequent extraction and/or purification of its endogenous FTFs are the main limiting factors. It is necessary to investigate the use of other native or recombinant hosts more appropriate for the high-level production and secretion of selected FTF enzymes.

As a result of the basic research carried out mainly to disclose the mechanism of fructan synthesis in plants, different papers have described the isolation of genes encoding FTF enzymes able to act on sucrose as substrate. Such genes have been isolated from different species, such as: *Cichorium intybus* (de Halleux and van Cutsem, 1997, Plant Physiol 113:1003), *Hordeum vulgare* (H°Chstrasser et al., 1998, FEBS Letters 440: 356-360), *Helianthus tuberosus* (Van der Meer et al., 1998, Plant J. 15:489-500), *Festuca arundinacea* (Luscher et al., 2000, Plant Physiology 124 (3):1217-1227, *Agave tequilana* (Avila-Fernandez et al., 2007, Plant Science 173: 478-486), *Allium cepa* (Vijn et al., 1998, Plant Physiology 117:1507-1513), *Lolium perenne* (Lasseur et al., 2009, Journal of Experimental Botany 57 (11):2719-2734) and *Triticum aestivum* (Schroeven et al., 2008, New Phytologist 180:822-831). Some of these genes have been expressed in *Pichia pastoris* for basic studies mainly aimed to characterize the substrate specificity, action mode and product profile of the enzymes in in-vitro experiments carried out at a laboratory scale (Altenbach et al., 2004, FEBS Letters 567: 214-218). In all the above reports, the alcohol oxidase I promoter (pAOXI) was used to induce the transgene expression in *P. pastoris*. The choice of this methanol-inducible promoter is disadvantageous for industrial scale processes due to the vast amount of methanol required during yeast fermentation. Methanol is flammable and highly toxic so its use is forbidden in food processing or food ingredients. In these researches the ability of the enzyme sucrose:sucrose 1-fructosyltransferase (1-SST) to synthesize 1-kestose was studied only at relatively low sucrose concentrations ranging from 0.1 to 0.15 M (34.2 to 51.3 g/L). This enzyme was also found capable to hydrolyze or further polymerize 1-kestose (Luscher et al., 2000; Plant Physiology 124 (3):1217-1227: Avila-Fernandez et al.; 2007 Plant Science 173: 478-486). Extremely low yields of the *Pichia*-produced 1-SST enzymes were achieved due to degradation and instability problems.

To date, there are no reports dealing with the use of plant enzymes, either native or recombinant, to produce 1-kestose from sucrose at industrial scale.

At industrial scale, only the juice of the plants *Cichorium intybus* and *Polymnia sonchifolia*, composed by a mixture of FOS of different DP where 1-kestose is not a major component, have been used (Guío et al., 2009, *Recent Patents on Food, Nutrition & Agriculture* Vol. 1 No. 3). Factors like the low yield, the low secretion to the extracellular medium, and the degradation by proteases during its expression by the recombinant deoxyribonucleic acid (DNA) technology, joined to the instability of the enzyme, have favored the use of fungi, or the enzymes FTF produced by them in the industrial production of FOS.

The use of constitutive promoters for the production plant FTFs in *P. pastoris* has not been reported. This is the most appropriate option for industrial scale production of recombinant enzymes with applications in the food industry.

Membrane bioreactors (MBR) are widely used for water recycling in buildings, wastewater treatment for small communities, industrial waste treatment, landfill leachate treatment, etc. (Judd S., 2008, Trends in Biotechnology 25 (2): 109-116). Only two reports describe the use of direct contact MBR for FOS production (Sánchez et al., 2008; Food and bioproducts processing 86, 109-115). In one of them, membranes are used to separate the microorganism from the reaction mixture containing FOS, wherein 1-kestose was not the major product. A similar bioreactor was used to remove, through a nanofiltration membrane, the glucose released (that inhibits FOS synthesis) by the non-immobilized *A. niger* ATCC 20611 β-fructofuranosidase in a batch reaction where the initial sucrose concentration was only 300 g/L and the product 1-kestose reached to represent 38.7% of the total FOS fraction (Nishizawa et al., 2001; Food Sci Tech res. 7.1 39-44). Under these conditions, the industrial production of 1-kestose would not be economically feasible. There are no papers or patents reporting the use of MBR to continuously produce 1-kestose from sucrose with the reuse of a soluble fructosyltransferase of any origin. It remains of great interest to develop methods and technologies for the cost-effective production of 1-kestose at industrial scale.

DETAILED DESCRIPTION OF THE INVENTION

The present invention solves the problem stated above by providing a method for industrial scale production of 1-kestose from sucrose, by a simple, cheap, efficient and industrially scalable technology. The method of the invention is characterized by the conversion of sucrose in to 1-kestose in a bioreactor where a recombinant FTF enzyme, isolated from *F. arundinacea*, and constitutively expressed in a non-saccharolytic yeast as recombinant host is employed.

The method, described for the first time in this invention, comprehensively addresses the solution of the main technological limitations existing in the process of FOS production from sucrose, particularly the limitations related to the production of 1-kestose. The procedure described has incidence in the two key stages of the process: 1) The production of the enzyme or biocatalyst, and 2) The production of 1-kestose.

For the purposes of the present invention, industrial scale is defined as the 1-kestose production scale in which the total or partial volume of the obtained product is commercially used. Current designed equipment available on the market can be used for these purposes.

Within the context of this invention, a non-saccharolytic yeast is defined as a wild-type or mutated yeast lacking endogenous activity that hydrolyzes or polymerizes sucrose. Some examples of these yeasts are: the methylotrophic yeasts *P. pastoris, Hansenula polymorpha* and the *Saccharomyces cerevisiae* yeast mutant YSH 2.64-1A (Rehm et al., 1998, Journal of Bacteriology 180 (5): 1305-1310).

In one embodiment of this invention the FTF is a sucrose: sucrose 1-fructosyltransferase (1-SST). In the invention the 1-SST obtained by recombinant DNA technology is so called 1-SSTrec. To optimize the stage of production of the enzyme, this invention started with a process of selection and identification of plant FTFs, 1-SST type, isolated from tall fescue (*F. arundinacea*), onion (*A. cepa*) and blue agave (*A. tequilana*), respectively. This approach was absent in the previous literature related to the industrial production of FOS. The genes encoding each of said enzymes were cloned in an expression cassette for the genetic modification of the yeast *P. pastoris*. In spite of the possible productive limitations of this yeast as a host for the industrial production, for example the limitation of dissolved oxygen during its growth, this yeast accomplishes the requirement of lacking endogenous enzymes capable to react on sucrose or fructans, and it is considered appropriate as a host for biotechnological purposes. *P. pastoris* can reach high biomass yields when grown under controlled conditions in fermentors, and it is renowned for allowing the production and secretion of high levels of heterologous proteins to the culture medium. The yeast has the GRAS status from the standpoint of biosafety regulations for food processing. Hence, the method of production of 1-kestose referred before, wherein the non-saccharolytic yeast is a *P. pastoris* strain, is part of this invention.

In a first step of this research, the alcohol oxidase I promoter (pAOXI) was successfully used to induce the transgene expression of 1-SSTrec. However, the use of this methanol-inducible promoter is not allowable for industrial scale processes due to the vast amount of methanol required during yeast fermentation. Methanol is also flammable and volatile. On the other hand, its use is forbidden in food processing or food ingredients. Surprisingly, the expression of the *F. arundinacea* 1-SST gene under the transcriptional control of the glyceraldehyde-3-phosphate dehydrogenase promoter (pGAP) did not cause cell toxicity, and allowed the production of high amounts of biomass and levels of expression of the enzyme secreted to the extracellular medium higher than the other two FTFs studied in the invention. This is the first report regarding to the use of this constitutive promoter for the expression of a plant FTF gene Three *P. pastoris* transformants from each of the above-mentioned constructs were evaluated for biomass production and fructosyltransferase activity in fed-batch fermentations. After yeast growth in 5-liter fermentors for 72 hours, the culture broths were centrifuged and two fractions were obtained: one fraction of intact cells or biomass, and the other fraction of culture supernatant. Both fractions were assayed to for enzymatic activity by incubation with a 0.87 M sucrose solution (300 g/L) in 0.02 M sodium acetate buffer, pH 5.5 at 30° C. during 30 minutes. In said conditions, the three transgenic yeast clones carrying the *F. arundinacea* 1-SST gene showed the highest levels of activity in both the intracellular and extracellular fractions, indicating an activity higher than the one observed for the rest of the analyzed enzymes. The 1-SSTrec isolated from *F. arundinacea*, surprisingly, was more stable that its homologues isolated from onion and agave, which allows the production of 1-kestose at big scale.

In an attempt to increase the yield of 1-SSTrec, multiple copies of the *F. arundinacea* 1-SST expression cassette were incorporated by double and single homologous recombination events in the genome of the host yeast after successive retransformation steps and massive screening of the clones for FTF activity. The gradual increase of the transgene dosage had an additive effect on 1-SSTrec yield without inhibiting cell growth. The elite clone named CIGB 308 contains at least nine gene copies stably integrated in the genome as determined in Southern blot experiments using the 1-SST coding gene and the 5' region of the resident AOX1 locus as hybridization probes. The observed hybridization patterns allow the precise identification of the multicopy *P. pastoris* strains, including the elite clone CIGB 308. Accordingly, a method for the production of 1-kestose at industrial scale wherein the strain of *P. pastoris* contains multiple copies of the gene encoding the 1-SST integrated in the genome is also an object of this invention.

When the *P. pastoris* strain CIGB 308 is cultured in a fermentor it produces the 1-SSTrec enzyme. This occurs when the fermentor is used with a discontinuous, a continuous or a fed-batch operation, using a culture medium supplemented with yeast extract, trace elements and vitamins, and employing glycerol or glucose as a carbon source. However, is preferred the use of sucrose or raw materials that contain it, since higher productive yields are obtained with said substrate.

Hence, in an aspect of the invention, the FTF employed in the production of 1-kestose at the industrial scale is obtained in the culture supernatant and/or the cell pellet of *P. pastoris*. In an embodiment of the invention the FTF is produced by culturing the recombinant yeast host in a fermentor used with a discontinuous, a continuous or a fed-batch operation. In a particular embodiment, the carbon source used for the yeast culture is a compound selected among glycerol, glucose and sucrose of any purity degree.

The extracellular 1-SSTrec activity achieved in this invention (~100.0 U/mL of cell-free culture supernatant) is rather similar to the average level reported for fungal enzymes (Driouch et al., 2010, Appl Microbiol Biotechnol 87:2011-2024) and it is much higher than the values described for FTF of different origins expressed in yeast (Trujillo et al., 2002; Affinity 59 (500): 365-370; Rehm et al., 1998, Journal of Bacteriology 180 (5): 1305-1310). Regarding the activity in the intracellular fraction, the combination of the high activity with the high cell density gives place to yields in biomass that go over the 38 000 U per culture liter, which is 6 or 7 times above the highest values reported in the literature for fungal enzymes (Dorta et al., 2006; *Journal of Industrial Microbiology and Biotechnology*. 33(12): 1003-1009).

In spite of the productive limitations of *P. pastoris* already mentioned, the selection of *P. pastoris* as the host for the recombinant expression of 1-SSTrec overcomes the technical limitations described above concerning the use of fungi as natural FTFs sources. On the other hand, from the point of view of biosafety regulations, *P. pastoris* is a GRAS organism for food processing.

In one embodiment of the invention, the sucrose conversion into 1-kestose at the industrial scale is performed using a substrate concentration higher than 400 g/L. In a particular embodiment of the invention, the conversion of sucrose in 1-kestose is done by free or immobilized 1-SST.

In an aspect of the invention, the conversion of sucrose in 1-kestose is performed in a membrane, fixed bed, or stirred tank bioreactor. In a particular embodiment, the membrane bioreactor is operated continuously or semicontinuously.

It is also an object of the present invention, an enzyme preparation for industrial sucrose conversion to 1-kestose comprising 1-SST, isolated from *F. arundinacea*, constitutively expressed in a non-saccharolytic yeast.

For the purposes of this invention, an enzyme preparation is defined as a liquid or solid formulation with enzymatic activity and able to react with a specific substrate transforming it into a product.

In one embodiment of the invention, the saccharolytic yeast used to obtain 1-SSTrec is a *P. pastoris* strain. In a particular embodiment, said *P. pastoris* strain contains multiple copies of the 1-SST coding gene integrated in its genome. From this yeast culture, 1-SSTrec is obtained in the culture supernatant and/or in the cell pellet. In line to the purpose of this invention, the 1-SST can be used in liquid or solid state, as a free or immobilized enzyme. In an embodiment of the invention, the concentration of sucrose that is employed in the industrial production of 1-kestose, by using the enzyme preparations comprising the 1-SST, is higher than 400 g/L.

As it is demonstrated in the examples of the application, the 1-SSTrec preparations, in liquid or solid state, in free or immobilized form, obtained from the culture supernatant or the cell biomass of *P. pastoris* CIGB 308 strain through conventional processes for purification, freeze drying and immobilization of proteins, displayed enough thermal stability to be stored and marketed without the need of refrigeration. Due to this characteristic, such preparations can be used finally as biocatalysts for industrial FOS production, giving place to the second stage of the method of production of 1-kestose of the invention. The enzyme preparations of the invention, in their different forms have in common that in the presence of sucrose as a substrate are capable of producing FOS with a conversion rate higher than 55%, where 1-kestose specifically constitutes more than 90% of the total FOS fraction.

In one embodiment of the invention, the 1-kestose synthesis reaction takes place under the following conditions: 200-800 g/L sucrose, preferably 600 g/L; pH 4.0 to 7.0, optimum 5.5; temperature 30-50° C., preferably 40° C.; enzyme/substrate rate 2-40 U/g for reaction times of 1 to 24 hours, preferably 15 U/g for 3-hour reactions. These conditions are applicable to liquid or solid 1-SSTrec preparations, disregarding the type of bioreactor and the operation mode used to produce FOS. The method of the present invention overcomes the limitations that reflect the state of the art regarding the process for industrial production of FOS, particularly 1-kestose. Instead of using fungi or fungal FTF, a recombinant plant enzyme is used, and said enzyme unexpectedly, and in contrast with other plant derived FTF, is stably secreted at high levels in *P. pastoris* and produces 1-kestose efficiently, as a result of its action on sucrose. Prior to the present invention, recombinant plant enzymes had not been used for industrial FOS production. On the other hand, in the stirred tank reactor technology, generally used for industrial enzymatic reactions, the enzyme is used only once, what is translated in a low productivity, variation in the product quality (due to lot to lot inconsistency), etc. In an invention embodiment, the use of in a membrane bioreactor, operating either in batchwise, continuous or sequential mode (preferably the latter) allows to increase the productivity, since in less time conversions similar to those obtained in a stirred tank reactor are achieved, and where more than 55% of sucrose is converted into FOS, with 1-kestose accounting for more than 90% of the FOS content. These results surpass previous reports and solve the limitations of the existing technologies for the industrial production of FOS, all based on the use of filamentous fungi. On the other hand, the method of the invention requires lower investment cost, lower energy consumption, reduced consumption of enzyme per amount of produced 1-kestose, and reduces the number of operations in the refining of the final product.

As stated before, applying the method of the invention the limitations present in the described FOS production processes, for any microorganism and any tipe of reactor, are overcome.

For the first time the 1-SST of *F. arundinacea* is used for the industrial production of 1-kestose. There are no reports of industrial production of FOS using a recombinant plant FTF. Unexpectedly, and unlikely from other plant FTFs tested, this enzyme is stably produced at high levels, and it is secreted into the culture medium of the host yeast *P. pastoris*. In addition to these technological advantages, the recombinant enzyme of the invention mainly produces 1-kestose, as a result of its action on sucrose at concentrations higher than 400 g/L.

The fungal enzymes also synthesize this trisaccharide, but use it almost from the beginning of the reaction as a substrate to produce 1-nistose and fructosylnistose, which attempts against the final yield of 1-kestose.

On the other hands, at present there are no providers of FTF for the mass production of FOS in the international market. The method of the invention creates a new procedure, of low cost, for the industrial production of a recombinant plant, which produce vast amounts of 1-kestose, facilitating the commercial availability of this type of enzymes. Surprisingly, the use of the recombinant FTF of *F. arundinacea* has as an additional advantage that makes cheaper the process to obtain FOS, particularly 1-kestose, in comparison to those described so far involving other FOS production technologies.

Hence, the invention provides a method to produce 1-SST at an industrial scale, characterized by the fact that the microorganism grown in fermentors is a non-saccharolytic yeast containing multiple copies of the gene coding for the *F. arundinacea* 1-SST integrated into the genome. The recombinant yeast expresses constitutively the 1-SST coding gene. In one embodiment of the invention, the non-saccharolytic yeast constitutively expressing the 1-SST coding gene is a *P. pastoris* strain. For the purposes of this invention, the recombinant 1-SST is harvested from the *P. pastoris* culture supernatant and/or the cell pellet.

For the purposes of the present invention, the industrial scale production of 1-SST is the scale that involves the culture in fermentors of a recombinant strain that produces 1-SST whose total or partial volume exceeds 10 000 U of enzyme.

Opposite to the reports found in specialized literature, in an embodiment of the invention, for the first time, the use of said plant FTF is combined with the utilization of a membrane bioreactor. This combination optimizes the process to obtain high yields of FOS and 1-kestose. The results obtained with said combination were surprising, with yield values higher than those theoretically calculated by mathematical models. Additionally, this process eliminates lot-to-lot inconsistencies and product variability found when other types of reactors are used. It allows the reuse of the soluble FTF and thereby it achieves feasible enzyme-substrate ratios, from a techno-economic point of view, that are 10 times higher than those used in stirred tanks. These two advantages are translated in to the reduction of the reaction times to 3 hours, increasing the productivity per day at least 5 times compared to the stirred tank, consequently lowering the production costs. Moreover, it reduces the manipulation steps and demands less physical area for the production process. Another aspect of the present invention is a product for human or animal feeding that comprises 1-kestose obtained by the method of the invention, which is characterized by the conversion of sucrose in 1-kestose in a bioreactor by using a recombinant FTF, isolated from *F. arundinacea*, constitutively expressed in a non-saccharolytic yeast host. In a particular embodiment, this product for human or animal feeding is formulated with probiotics in symbiotic preparations to be used as a nutraceutical.

EXAMPLES

Example 1. Comparative Study of Fructosyltransferase (FTF) Activity Levels Displayed by Three Sucrose:Sucrose 1-Fructosyltransferase (1-SST) from Plants Produced in *Pichia pastoris*

To compare the FTF activity levels of the three enzymes mentioned above, the cDNAs encoding the 1-SST enzyme from tall fescue (*Festuca arundinacea*), onion (*Allium cepa*), and blue agave (*Agave tequilana*) were isolated from its native hosts via Reverse transcription (RT)-Polymerase Chain Reaction (PCR) using primers previously described in the literature [Vijn et al. 1998, *The Plant Journal* 11:387-398; Luscher et al. 2000, *Plant Physiology* 124:1217-1227; Avila-Fernandez et al. 2007, *Plant Science* 173:478-486].

The amplified PCRs products corresponding to the DNAs coding for the mature enzyme (Sizes: 1-SST fescue: 1668 bp, 1-SST onion: 1668 bp and 1-SST Agave: 2026 bp) were fused at its 5' end, following the correct reading frame, to the *S. cerevisiae* a factor signal peptide and at the 3'end to the sequences encoding both, the myc epitope and six histidine residues tag present in the commercial vector pGAPZ a C (Invitrogen, Leek, Holland). This commercial vector allows selection of the resulted transformants by resistance to the antibiotic zeocin.

Figure 1:
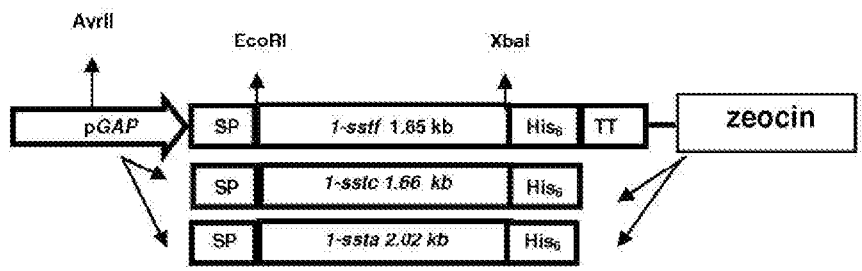
FIG. 1. Graphic representation of the expression cassettes resulting from the insertion of the genes encoding the respective 1-SST enzyme from tall fescue (1-sstf), onion (1-sstc) and blue agave (1-ssta) in the vector pGAPZαA,B,C. The corresponding plasmids were named as p1-SSTF (tall fescue 1-SST), p1-SSTC (onion 1-SST), and p1-SSTA (blue agave 1-SST), respectively. $P_{GAP}$: GAP promoter, SP: α-factor signal peptide of *Saccharomyces cerevisiae*, $His_6$: polyhistidine tag, TT: AOX1 transcription terminator of *Pichia pastoris*.

In the three obtained constructs, called p1-SSTF (fescue 1-SST), p1-1SSTC (onion 1-SST) and p1-SSTA (1-SST agave), the chimeric genes coding for three 1-SSTs were placed under the transcriptional control of the GAP promoter and the transcriptional alcohol oxidase 1 terminator (AOX1TT), as shown in FIG. 1.

The three constructs were digested at the single AvrII restriction site in the GAP promoter and introduced by electroporation into the genome of the X-33 host yeast strain. As a result, about 20 transformants were obtained for each construct after grown on YP medium supplemented with 2% glycerol and Zeocin 100 mg/mL. For the comparative study, 3 Zeocin resistant clones of each of the three variants were grown in a 5 liter (effective volume) fermenter up to reach the cells stationary phase.

Each fermenter was in°Culated with 200 mL of each clone inoculums previously grown in a shaker.

To maintain the dissolved oxygen values above 20% in the first stage of the fermentation, agitation was increased automatically from 500 to 900 rpm, and aeration was kept at 1 vvm (volume of air/volume of medium/minute). Once increased the value of dissolved oxygen, indicative of glycerol depletion, the second feed stage started.

To start the second stage, the air flow increased to 2 vvm and the culture was fed with 1.5 L of increment solution (with the same initial carbon source) at a flow rate between 5 and 7 mL/L/h controlled by variations of dissolved oxygen values. No toxic effects were observed during the 72 hours of cultivation for the recombinant or wild type strains grown under similar conditions.

Then, the final culture was separated by centrifugation to produce two fractions, a cell pellet (or biomass) and a culture supernatant. Samples of 0.2 mL of both fractions reacted for 30 minutes with a sucrose solution to 300 g/L (0.87 M). The concentration of liberated glucose as a result of the transfructosylation reaction over sucrose was used as indicative of the activity level of the recombinant clones FTF. The intensity of the transfructosylation reaction was established from a calibration curve which relates the color variations in samples to defined amounts of glucose. A relative high activity (sample color turned red with intensity equivalent to glucose concentrations above 5.5 mM) was observed in the 30-min reactions of the intact cells and the culture supernatant samples from the three clones expressing the tall fescue 1-SST gene. By contrast, none of the clones carrying either the onion 1-SST gene or the blue agave 1-SST gene showed detectable activity in the 30-min reactions. A slight activity was evident (shift of sample color to light pink being equivalent to glucose concentrations in the range 0.5-5.5 mM) only after the longer incubations for 3 and 5 h.

Example 2. Mean Values of the Parameters Analyzed During Fermentation Run of the Three Single 1-sstf Gene Copy Clones with High FTF Activity The three clones carrying a single 1-sstf copy incorporated in its genome were compared at the fermenter level, using the same experimental conditions described in Example 1.

TABLE 1

Comparison of the evaluated parameters obtained during the fermentation of the three clones with high 1-SSTrec activity

| Parameter | Value |
| --- | --- |
| Biomass yield (g/L of culture) | 366 ± 4 |
| 1-SSTrec Intracellular activity (U/g of wet biomass) | 4.3 ± 0.2 |
| 1-SSTrec Extracellular activity (U/L of culture supernatant) | 3.7 ± 0.1 |
| Culture time (Hours) | 69 |
| Total 1-SSTrec activity (U/L of culture) | 3955 ± 211 |
| Total 1-SSTrec activity in the Biomass (U/L de cultivo | 1573.8 ± 25.6 |
| Productivity of biomass Activity (U/L/h) | 22.8 |

One 1-SSTrec unit (U) represents the amount of enzyme which releases 1 micromol of glucose per minute when react with a 50% (1.46 M) sucrose solution in sodium acetate buffer 0.1 M (pH 5.5) for 30 minutes at 30° C. The data shown in Table 1 represent the average of the evaluated parameters values obtained in the three fermentations corresponding to each tested clone ±a standard deviation.

The productivity of these three clones was 2-fold higher when using the constitutive expression system than that obtained with the methanol inducible system due to a higher concentration of cells (366 g/L) was reached in a shorter culture time (69 hours).

Example 3. Increased 1-SSTrec Activity by Integration of Multiple Copies of the 1-sstf Gene Expression Cassette in the *Pichia pastoris* AOX1 Locus To develop an economical industrial production technology to produce FOS, high levels of 1-SSTrec activity are required therefore, the need to increase the gene dosage in the host yeast is needed.

To obtain multiple copies in tandem of the expression cassette, the plasmid p1-SSTF which contains only one copy of the expression cassette containing the gene 1-sstf in its genome was digested, with the restriction enzymes BamHI and BglII. The resulted 2.82 kb band containing the expression cassette was isolated from agarose gel and religated using T4 ligase.

Joining by T4 ligase of BamHI (G-GATCC) and BglII (A-GATCT) restriction sites, generates a hybrid site with GGATCT sequence, which is not recognized by any of these two enzymes. During the ligation reaction these two enzymes, BamHI and BglII, were added to facilitate the connection of different ends. The 5.64 kb band containing two copies of the expression cassette was isolated and treated again with BamHI and BglII enzymes to ensure that the expression cassettes are joined in the same transcriptional direction.

This sequence was inserted into the same plasmid p1-SSTF BamHI digested and dephosphorylated with alkaline phosphatase. The new built construction (p1-SSTF3x) carries three copies in tandem of the expression cassette. The p1-SSTF3x was digested with the enzymes BamHI and BglII, the 8.46 kb band was isolated and religated obtained as described in the previous step. The 16.92 kb sequence was inserted into the pAO815 vector, BamHI digested and dephosphorylated with alkaline phosphatase.

Figure 2:
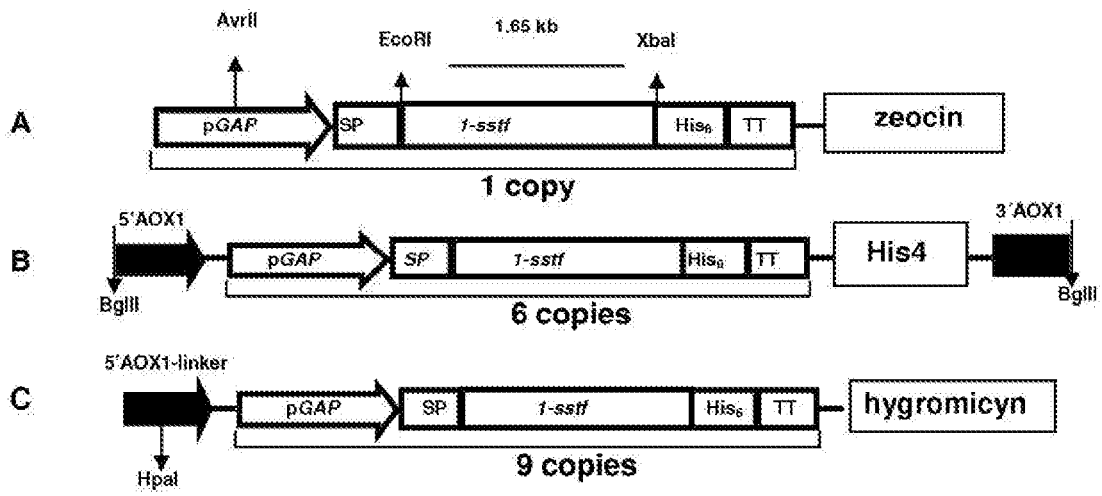
FIG. 2. Strategies used in the construction of plasmid p1SSTF6x+6 additional copies of the expression cassette for constitutive high-level expression of the 1-sstf gene in the *Pichia pastoris* strain GS115. A. Construction with one gene copy. B. Construction with six gene copies, selection by histidine4 gene complementation C. Construction with nine gene and hygromycin resistance. $P_{GAP}$: GAP promoter, 5'AOX1: promoter of alcohol oxidase, SP: α-factor signal peptide of *S. cerevisiae*, $His_6$: polyhistidine tag, TT: AOX1 transcription terminator, His4: non-mutated histidine4 gene.

This vector allows selection of *P. pastoris* GS115 transformants by complementation of the his4 auxotrophy. The resulting plasmid (p1SSTF6x) contains six copies of the expression cassette arranged in tandem and in the same transcriptional direction, inserted between the AOX1 promoter and a 3' fragment of the AOX1 locus terminator region of (FIG. 2).

This plasmid was BglII digested for transformation by electroporation of *P. pastoris* GS115 strain. With this digestion, two fragments, one yielding a 22.23 kb band carrying in the center six expression cassettes in tandem and the gene complementing auxotrophy generated by his4, at the 5'end is the AOX1 promoter and in the 3' end a 3' fragment of the terminator region of the AOX1 locus.

With this strategy the double homologous recombination that replaces the AOX1 locus is favoured. Colonies of the GS115 strain transformed with plasmid p1-SSTF6x were selected on minimal YNB medium supplemented with 2% glucose. In order to evaluate the ability of the transformants to use sucrose as a carbon source, 93 colonies His4+were grown individually in a 100-well YP agar plate (pH 5.5) supplemented with 5% sucrose and a pH indicator, bromothymol blue 0.025%.

The GS115/p1-SSTF clone, with a single 1-sst gene copy (PF1x) was used as positive control for this experiment. Two clones named PF6Xb PF6Xa turned the medium color from the initial green (pH 5.5) to yellow (pH≤6.0), due to the 1-SSTrec transfructosylation reaction over sucrose that yielded lactic acid due to consumption by the microorganism of the released glucose from sucrose. This colour change of the medium °Ccurred more quickly in the multicopy strains that in the strain carrying a single gen. This fact indicates that multicopy clones displays greater enzymatic activity than those carrying a single gene copy.

To corroborate this result, PF6Xb PF6Xa multicopy clones, and the simple copy PF1x, were grown in 10 mL of liquid YP medium supplemented with 2% glycerol in orbital shaker for 24 hours at 28° C. Glucose released due to the FTF activity of the recombinant enzymes in the fractions corresponding to the pellet (biomass or cells) and the culture supernatant of both, multicopy clones and the single copy clone as well as was determined by the "glucose-Trinder" (Sigma) kit based on colorimetric reaction of the oxidase/peroxidase/glucose chromogenic enzyme complex in the same way as explained in Example 1.

The two multicopy clones showed higher enzyme activity than that displayed by the simple copy (Table 2), demonstrating that increased copies of the 1-sstf gene integrated into the *P. pastoris* genome increased 1-SSTrec activity in these two recombinant strains. The clone PF6Xb showed a 31.4% of 1-SSTrec activity in the culture supernatant greater than the PF6Xa clone and 64.2% greater than the single copy done. In the biomass, clone PF6Xb had a 18% of enzyme activity greater than PF6Xa clone and 36% greater than the single copy clone.

Table 2 shows the effect of the 1-sstf gene copy number on enzymatic activity of the multicopy *P. pastoris* clones. As controls the strain GS115, and the single copy clone were used. Different letters to the right of the data indicate significant differences determined by a simple Classification ANOVA using the statistical package StatGraph3. The mean values of enzyme activity (n=3) were compared using the Tukey HSD test ($p<0.01$).

TABLE 2

Comparison of 1-SSTrec Activity in single-and multicopy clones

| | Specific enzimatyc activity (×10⁻³ UAE/D.O$_{600}$) | |
| --- | --- | --- |
| Strain | Biomass (B) | Culture supernatant (S) |
| GS115 | 0.1081 ± 0.0015[d] | 0.1523 ± 0.0017[d] |
| PF1X | 2.5813 ± 0.0012[c] | 4.7830 ± 0.0015[c] |
| PF6Xa | 4.9717 ± 0.0020[b] | 9.1545 ± 0.0021[b] |
| PF6Xb | 7.3548 ± 0.0014[a] | 13.3512 ± 0.0016[a] |

Units of enzyme activity/optical density measured at a wavelength of 600 nm (UAE/D.O$_{600}$). Different letters denote significant differences between the enzyme activities compared to each other by using the Tukey HSD test ($p<0.01$).

According to the results obtained above, the multicopy clone PF6Xb showed the highest 1-SSTrec activity in both, the biomass and the culture supernatant so that, it was chosen for further expression experiments. From now, this selected clone was re-named as PF6X.

Example 4. Increased 1-SST Activity by Retransformation of the PF6X Multicopy Clone by Insertion of Six Additional Copies of the Expression Cassette in the AOX1 Locus To increase the enzymatic activity of clone 1-SST PF6X a new plasmid was built called pALS223. To obtain this new construction, the 16.92 kb sequence containing six copies of the expression cassette in tandem and in the same transcriptional direction used to construct the plasmid p1-SSTF6x, was inserted into the vector pPICHaC AOX1-linker previously digested with BamHI and dephosphorylated with alkaline phosphatase.

This vector allows single homologous recombination in the *P. pastoris* AOX1 promoter and further transformants selection with the antibiotic hygromycin. After checking this genetic construct by restriction analysis and DNA sequencing, we pr°Ceeded to linearize this new plasmid with the enzyme Hpa I and retransform PF6X clone with this new construct through PF6X cells electroporation. This enzyme cuts in a specific site of the AOX1 promoter, which promotes integration into the yeast genome by simple homologous recombination at the AOX1 locus.

Transformants with more than 6 copies of the expression cassette inserted in the host yeast genome were selected in solid YP medium supplemented with hygromycin 2% glycerol 0.2 g/L. Enzymatic activity in the biomass and in the culture supernatant to more than 60 hygromycin (HigR) resistant colonies was determined using the colorimetric reaction of the enzyme complex glucose oxidase/peroxidase/chromogen reagent kit "glucose-Trinder. In this assay also were included the PF6x and PF1x strains as controls.

One hygromycin-resistant clone called CIGB 308, showed the highest 1-SSTrec enzyme activity in both, the cell pellet and the culture supernatant. This new clone showed higher enzyme activity in the supernatant (1.87 times) and biomass (1.76 times) than PF6X strain.

When comparing with the single copy strain, 1-SST activity displayed by clone CIGB 308 was 3.58 times higher in the supernatant, and increased 2.41-fold in the biomass, thus confirming that increasing the copy number of the 1-sstf gene stably integrated in the host, also increases 1-SST activity in the yeast host. Southern blot analysis revealed that in clone CIGB 308 were stably integrated 9 copies of the expression cassette. These results indicate that in the event of retransformation Inserted only 3 copies of the expression cassette instead of 6 as expected.

Example 5. The *P. pastoris* GIGB 308 Strain has More 1-SST Enzymatic Activity and Display More Productivity than its Predecessors PF1X and PF6X at Fermenters Scale The *P. pastoris* CIGB 308 clone and their precursors, with one and six genomic integrated copies of the expression cassette (PF1X, PF6X) respectively, were grown in 7.5 L fermenters with 5 L working volume at 28° C., pH 5.5, 500-900 rpm, aeration 1.2 vvm, and controlled dissolved oxygen above 20%. Regardless of the different integrated copy number of the expression cassette, the three recombinant strains, showed a similar growth pattern.

After 19 and 20 hours of growth, the initial glycerol content depleted, while the dissolved oxygen pressure was controlled up to 20% by gradually increasing the agitation from 500 to 900 rpm. With the glycerol depletion, there was a rapid dissolved oxygen rise and then started the culture feeding with 50% glycerol (v/v), during the 72 hours of the fermentation process.

Under these culture conditions, the overall biomass obtained from the three compared clones was 358±8 g/L wet weight, so it can be inferred that the gene dosage, as well as the production and accumulation of the recombinant enzyme, did not affect growth and was no toxic to the yeast host.

Just after 70-72 hours of culture GIGB 308 clone showed the highest extra- and intracellular 1-SST activity, reaching a maximum of 29.7±0.2 U/mL of culture and 12.4±0, 2 U/mL of culture (34 U/g wet weight), respectively. From the overall 42.1±0.2 U/mL detected after the 308 CIGB growth, 70.6% of the FTF activity was found in the culture supernatant and 29.4% in the cells. From the results obtained in this comparative study we decided to choose the CIGB 308 clone for the mass production of 1-SSTrec.

At the time of this invention there were no reports in the literature describing the fermentation strategy to obtain a plant 1-SSTrec constitutively expressed from a multicopy *P. pastoris* clone.

Example 6. Incremented Culture Strategy for the *Pichia pastoris* CIGB 308 Strain Growth Using Sucrose as a Carbon Source The fermentation cost of *P. pastoris* CIGB 308 strain is reduced using a cheaper carbon source other than glycerol, such as sucrose or glucose. *P. pastoris* GS115 strain, which is used as host has no invertase activity, so it can not use sucrose as a carbon source. However, due to the new FTF activity acquired by the yeast host glucose is released as consequence of the 1-SSTrec transfructosylation reaction from sucrose and then it is metabolized directly for the growth of the recombinant yeast host. This behaviour of the recombinant yeast strain allow the reduction of the fermentation costs during the production process.

Sucrose fermentation in a batch increased culture was performed in a 75 L fermenter capacity with 50 L working volume. The adjusted parameters were: Temperature: 28° C., pH 5.5 Agitation: 600 rpm. Aeration: 1.0 vvm. Operating pressure: 0.2 atm. The carbon source used was sucrose at 50 g/L, contained either in refined sugar, raw sugar or honey.

With the carbon source depletion (detected by increased pH or increasing the pressure of oxygen), at approximately 20 hours after fermentation starting, the increment solution was added (solution of the same carbon source initially used, but 500 g/L) at a rate of 8 mL/L/h increment by initial culture volume. Then, fermentation parameters were readjusted as follow: Agitation: 800 rpm, aeration 1.5 vvm, oxygen pressure: 0.4 atm. The fermentation was performed during 72 h.

With these culture conditions the reached biomass yields were similar to those achieved with this same done but grown in glycerol medium. On the other hand, total enzyme activity (within 72 hours of culture) was by far superior to the sucrose-containing media regardless of the used raw material-containing sucrose. Growth results of the *P. pastoris* 308 CIGB strain, using different carbon sources, are summarized in Table 3.

TABLE 3

Summary of the results obtained after *P. pastoris* CIGB 308 strain growth in fermenters using glycerol or sucrose as carbon source.

| Carbon source | Extracellular Activity (U/mL of cell free supernatant) | Intracellular activity (U/ml of culture) | Total U/ mL culture | Wet XWeight (g/L) |
| --- | --- | --- | --- | --- |
| Glycerol | 29.7 ± 0.2 (70.6%) | 12.4 ± 0.3 (29.4%) | 42.1 ± 0.4 | 361 ± 4 |
| Refined sugar | 101.6 ± 9.5 (62.02%) | 38.9 ± 5.4 (37.98%) | 102.4 ± 11.3 | 375 ± 9 |
| Raw sugar | 53.9 ± 3.3 (46.3%) | 39.9 ± 2.9 (53.7%) | 74.2 ± 3.1 | 363 ± 4 |
| Honey B | 110.7 ± 0.2 (58.5%) | 49.6 ± 5.1 (41.5%) | 119.6 ± 6.3 | 368 ± 14 |

Values in parentheses represent the percentage of intracellular and extracellular enzymatic activity of the *P. pastoris* CIGB 308 strain after 72 hours of culture. An enzyme unit (U) represents the amount of 1-SSTrec which liberates 1 micromol of glucose per minute at initial vel°Cities of the reaction in a sucrose solution in 1.75 M sodium acetate buffer 0.1M pH 5, 5, to 30° C. The data represent the mean of the fermentations conducted with each of the carbon sources ±standard deviation.

According to these results it was concluded that both sucrose and honey are suitable substrates to undertake industrial production of this recombinant FTF.

Example 7. 1-SSTrec Enzyme Production in Continuous Culture

There are no reports in the literature describing the continuous production of recombinant FTFs expressed at high levels in *P. pastoris*. Continuous production of 1-SSTrec was performed in a 7.5 L INFORS HT fermenter with total working volume of 5 L. The following parameters were established and recorded throughout the culture, through Iris V 5.0 Software: The temperature was maintained at 28° C., while the pH value of 5.5 was controlled by automatic addition of $NH_3OH$ (28% (v/v)) and $H_3PO_4$ (40% (v/v)). The dissolved oxygen was maintained throughout the culture above 20% by automatically varying the agitation (between 500 and 900 rpm), air flow (1-2 vvm) and the pressure (0-0.7 atm).

The initial volume was 3 L fermentation medium containing 22 g/L $NH_4SO_4$, 18.2 g/L of $K_2HPO_4$, 7.5 g/L of $MgSO_4$ $7H_2O$, 0.5 g/L of $CaCl_2$ $2H_2O$; yeast extract 5 g/L, trace salts and vitamins in sufficient amounts plus sucrose 50 g/L. For discontinuous increase stage used 1.5 L of a solution of sucrose 500 g/L. In the stage of continuous culture was used a medium containing 200 g/L sucrose, yeast extract 2.5 g/L, 11 g/L $NH_4SO_4$, 9.1 g/L of $K_2HPO_4$, 3.75 g/L of $MgSO_4$, $7H_2O$, 0.25 g/L of $CaCl_2$ $2H_2O$; salts trace and vitamins.

The fermenter was Inoculated with 200 mL of inoculums previously grown in a shaker. Once exhausted the carbon source, the discontinuous increment stage started and the culture was fed at a flow rate ranging between 7 to 30 mL/L-h. With the increment depletion, the continuous culture started by feeding the bioreactor with a 1 day-dilution speed (D). After reaching the steady state, the culture operating was kept for 45 days, with an average activity yield of 70±5 U/mL and a cell concentration of 352±11 g/L wet weight.

Example 8. Determination of the Optimal Reaction Parameters of 1-SSTrec for the Synthesis of 1-Kestose The enzyme preparation obtained in the fermenter supernatant was subjected to a filtration process using a Sarticon Slice 200 (Sartorius) filter with a Hydrosart membrane (0.2 μm), following the manufacturer's instructions. Subsequently, the filtrated was concentrated 10 times by diafiltration, using the same equipment but with a Hydrosart ultrafiltration membrane (10 kDa) against sodium acetate buffer 0.1M to give a final preparation of 1000 U/mL. Optionally, the filtrate was subjected to a lyophilization process to obtain a solid enzyme preparation with an activity greater than 8500 U/g.

a) Determination of the Optimal pH for 1-SSTrec Activity:

The 1-SSTrec activity was examined in a pH range between 4 and 8. The reaction was performed for 1 hour at 30° C. in a 0.87 M sucrose solution and 10 U of enzyme in a final volume of 0.5 mL. For the pH range of 4.0 to 5.5 a sodium acetate buffer 0.1M was used, and for pH between 6.0-8.0 0.1 M phosphate buffer The maximum values of 1-SSTrec enzymatic activity was found at pH values between 5.5 and 6.0.

b) Temperature and Optimum Substrate Concentration for FOS Synthesis:

For the determination of these parameters, 60 U of 1-SSTrec reacted in buffer 0.1 M sodium acetate, pH 5.5 with substrate concentrations ranging between 200 and 600 g/L, at 30, 40 and 50° C. respectively, in a final reaction volume of 10 mL at 250 rpm. After 1 hour of reaction, sugars composition in the reaction mixture was determined by HPLC. For this chromatography 20 μl of the sample were applied in a Aminex HPX 42-C (BioRad, Richmond) column, with a work flow of 0.6 mL/min, a pressure of about 52 bar and a working temperature of 81° C. The mobile phase used was water and a refractive index detector— Knauer Differential Refractometer was employed. Sugars were quantified using the Biocrom software package, version 3.0, IGBC, 1996-1997.

Table 4 shows the composition and quantification (%) of sugars determined for different reaction conditions, the rate of 1-kestose synthesis and the relationship between transfructosylation and hydrolytic activity. The maximum rate of 1-kestose synthesis with no hydrolytic activity was reached at 40° C. and a sucrose concentration of 600 g/L.

Similar results were obtained when intact cells with 1-SST periplasmic activity, or immobilized cells in calcium alginate or the immobilized enzyme covalently joint to Eupergit (Sigma) were used as enzymatic preparation for sucrose conversion to 1-kestose.

TABLE 4

Influence of temperature and substrate concentration in the FOS synthesis

| Temperature | G | F | GF | $GF_2$ | $GF_3$ | $r_{(GF2)}$ | $R_{T/H}$ |
|---|---|---|---|---|---|---|---|
| 200 g/L | | | | | | | |
| 30° C. | 16.0 | 0.5 | 39.6 | 45.8 | 0.8 | 1.0 | 88 |
| 40° C. | 13.1 | 0.9 | 41.2 | 43.7 | 1.1 | 1.0 | 50 |
| 50° C. | 1.5 | 0.0 | 91.2 | 6.7 | 0.0 | 0.1 | — |
| 400 g/L | | | | | | | |
| 30° C. | 11.8 | 0.1 | 58.0 | 29.9 | 0.3 | 1.3 | 585 |
| 40° C. | 11.0 | 0.4 | 48.6 | 39.3 | 0.8 | 1.0 | 111 |
| 50° C. | 2.4 | 0.0 | 86.3 | 11.1 | 0.0 | 0.5 | — |
| 600 g/L | | | | | | | |
| 30° C. | 6.9 | 0.0 | 67.5 | 25.5 | 0.0 | 1.8 | — |
| 40° C. | 9.9 | 0.0 | 54.7 | 34.7 | 0.8 | 2.4 | — |
| 50° C. | 7.3 | 0.0 | 64.8 | 27.9 | 0.0 | 1.9 | — |

Composition of the reaction mixture after one hour of reaction (G), glucose (F), fructose (GF) sucrose, ($GF_2$) 1-kestose ($GF_3$) nystose. Reaction parameters ($r(GF_2)$) Speed synthesis of 1-kestose given in g/min (RT/H) Ratio transfructosylation and hydrolytic activity given by the ratio of 1-kestose and fructose composition.

c) Half-Life of Free and Immobilized 1-SSTrec:

Thermal stability was evaluated for free and Eupergit immobilized enzyme and for *P. pastoris* CIGB 308 cells immobilized in calcium alginate. Both, free or immobilized forms were incubated in 0.1 M acetate buffer, pH 5.5, at 30, 35 and 40° C. Samples were taken from each reaction with 24 hour intervals for 30° C., 1 hour for 35° C. and 20 minutes for 40° C., respectively, to test the residual activity. Subsequently, the half life time was defined as the time at which each of the assayed enzyme preparations had lost 50% of its initial activity. The results in Table 5 show that enzyme preparations containing free 1-SSTrec are much more stable than cells with 1-SST activity immobilized in calcium alginate Moreover, unexpectedly, the average life time of the crude extract in solution of 1-SSTrec at 30° C., under non-reactive conditions, is 1432 hours. This time exceeds more than 100 times the half-life times reported to date for plants enzymes 1-SST type.

TABLE 5

Half-life time of different 1-SSTrec preparations under non-reactive conditions

| | Half life time (hours) | | |
|---|---|---|---|
| Enzymatic preparation | 30° C. | 35° C. | 40° C. |
| Free 1-SSTrec (crude Extract) | 1432.0 | 6.1 | 0.7 |
| *P. pastoris* CIGB 308 cells immobilized in calcium alginate | 36.0 | 4.2 | 0.3 |
| Eupergit immobilized 1-SSTrec | 1856.0 | 12.9 | 1.6 |

A thermal stability test was performed to the lyophilized enzyme preparation. The result was that the solid preparation has a half-life time greater than three years at 30° C.

Example 9. Sucrose Transformation to FOS Catalyzed by the 1-SSTrec in a Batch Reaction Using a Stirred Tank Reactor The time course of FOS synthesis catalyzed by 1-SSTrec was conducted at sucrose concentration of 600 g/L, adding an enzyme—substrate weight ratio of 15 U/g in buffer 0.1M sodium acetate, pH 5.5; at 40° C., for 6 hours in a 1 L reactor at 250 rpm. Quantification and composition of the produced sugars was determined in samples picked every 20 minutes by HPLC similarly to Example 8.

Figure 3:
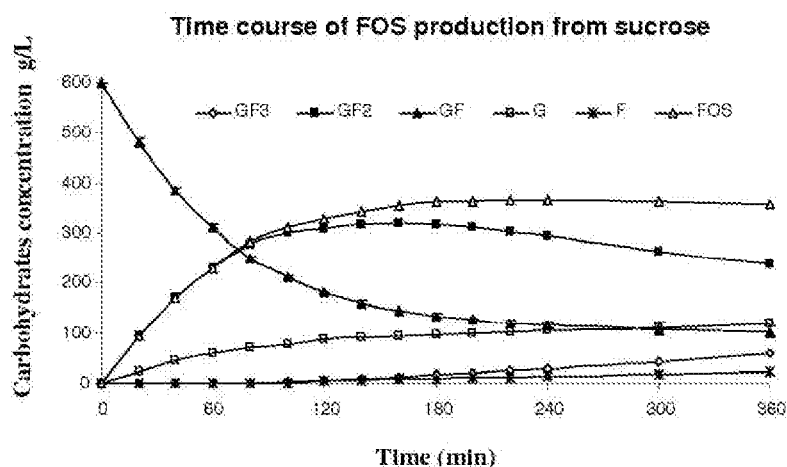
FIG. 3. Time course of FOS synthesis by the enzyme 1-SSTrec in a batch stirred tank reactor. Reaction conditions: 1-SSTrec 9000 U/L, sucrose 600 g/L in 0.1 M sodium acetate buffer (pH 5.5); temperature 40° C., stirring speed 250 rpm, reaction time 6 h. Legend: 1-kestose ($GF_2$); nystose ($GF_3$), total FOS (FOS=sum of $GF_2$ and $GF_3$); sucrose (GF); glucose (G); fructose (F).

Maximum production of 1-kestose was 320.8 g/L, 53.4% of the total carbohydrates in the mixture and 90.4% of total FOS. FIG. 3 shows that the maximum production of 1-kestose was reached between 2.7 and 3 hours of reaction, when over 70% of the initial sucrose was consumed. At this point matches the maximum concentration of 1-kestose with the onset of the appearance of the tetrasaccharide nystose.

Figure 4:
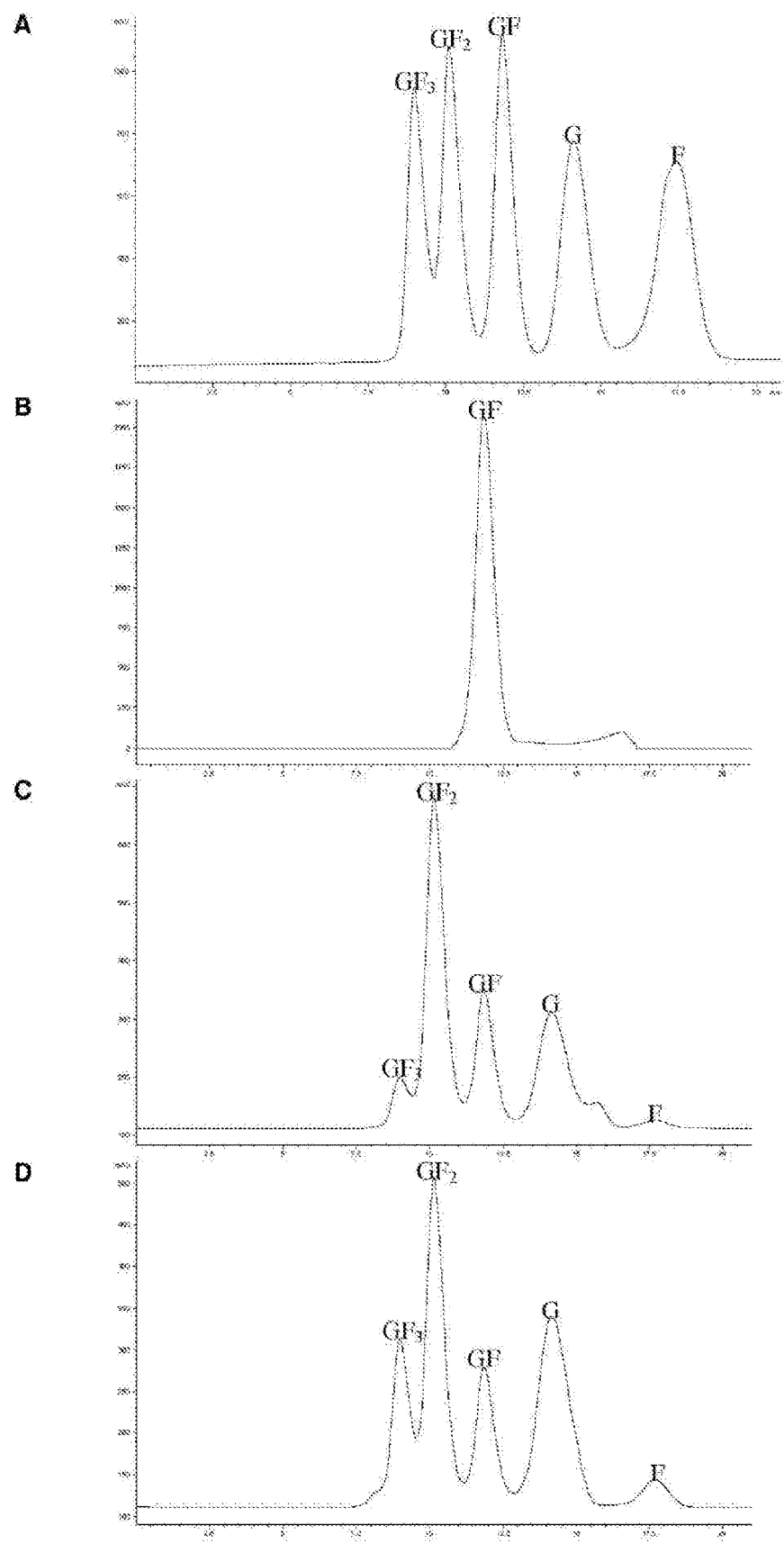
FIG. 4. HPLC chromatograms showing the product profile in samples retrieved at different reaction times ($t_r$). A. A mixture of the standards nystose ($GF_3$), 1-kestose ($GF_2$), sucrose (GF), glucose (G), and fructose (F). B. FOS synthesis by the 1-SSTrec at reaction time $t_r$=0. C. $t_r$=180 minutes. D. $t_r$=360 minutes.

This fact is advantageous for the use of 1-SSTrec in the large scale production of 1-kestose since not synthesized nystose in the transformation reaction of sucrose appears until 50% of initial sucrose is consumed as seen in FIG. 4. By contrast, the fungal FTF accumulates nystose from the start of the reaction with the synthesis of the first 1-kestose molecules and also synthesize the pentasaccharide fructosylnystose.

Similar values and behaviour of the course of sucrose transformation into 1-kestose were obtained using cells with periplasmic 1-SSTrec activity, free or immobilized in calcium alginate or 1-SSTrec covalently immobilized to Eupergit (Sigma) under similar reaction conditions. Table 6 shows the FOS concentration obtained by different enzyme preparations.

TABLE 6

Concentration of synthesized FOS after 3 hours of reaction using different 1-SSTrec enzyme preparations.

| Synthesized FOS | Free 1-SSTrec | Cells immobilized in calcium alginate | 1-SSTrec immobilized on Eupergit |
|---|---|---|---|
| total FOS | 354.7 g/L | 330.5 g/L | 342.2 g/L |
| 1-Kestose | 320.8 g/L (90.5%) | 322.1 g/L (97.4%) | 318.3 g/L (93.0%) |
| Nistose | 33.9 g/L (9.5%) | 8.4 g/L (2.6%) | 23.9 g/L (7.0%) |

The transfructosylation reaction mixture obtained after 3 hours of synthesis, was subjected to a pasteurization process so, the enzyme was inactivated. Subsequently, the syrup was subjected to a polishing process that began with a filtration, followed by demineralization, decolourization, concluding with a chromatographic separation for simulated moving bed (SMB), that after elution yielded a rich FOS stream with more than 90% of 1-kestose. This fact demonstrates the technical feasibility of this procedure to produce a 1-kestose rich syrup, the FOS with the highest prebiotic effect and so, becoming in the most commercial one.

Technical feasibility of this procedure at industrial scale, was confirmed through the scaled up of the transformation reaction from sucrose to 1-kestose in 30 and 100 L capacity reactors, respectively. The scaled up of this operation was performed by the method based on the "Principle of Similarity", from the information obtained in the tests performed in the 1 L model reactor. The concentration of 1-kestose obtained in the two new scales averaged 322±7 g/L. This result shows no significant difference with those obtained in the model reactor. This fact also demonstrated that the conversion reaction from sucrose to 1-kestose catalyzed by 1-SSTrec in stirred tank reactors is reproducible at higher scales.

Figure 5:
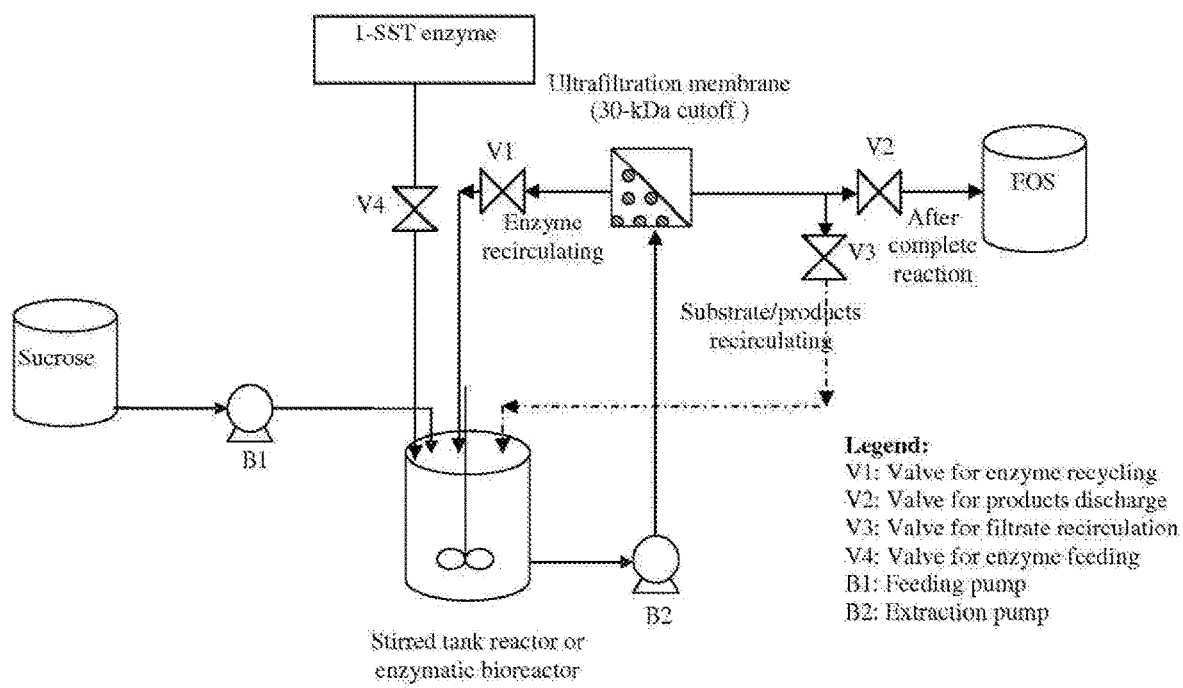
FIG. 5. Schematic representation of the system designed for FOS production in a membrane bioreactor.

Example 10. 1-Kestose Synthesis from Sucrose in a Membrane Bioreactor Operated Semicontinuously The procedure described in Example 9, for 1-kestose synthesis from sucrose by employing free 1-SSTrec in a stirred tank bioreactor was followed. For this purpose 1 L (working volume) stirred tank bioreactor was coupled in its output with a cartridge type ultrafiltration membrane (Prep/Scale TFF-1 30 kDa, Millipore, with nominal filter area of 0.09 m$^2$), allowing separation of the reaction products and the enzyme as shown in FIG. 5.

The parameters used were: 9000 U/L, initial enzyme concentration, initial sucrose concentration 600 g/L in 0.1 M acetate buffer, pH 5.5, temperature 40° C., 250 rpm stirring speed, flow bioreactor output feeding the membrane was 40 mL/min.

During the synthesis step, both, the retentate and permeate flow at the outlet of the membrane return to the enzymatic bioreactor. Every 30 minutes samples of the permeate stream were analyzed by HPLC in order to determine the conversion ratio of sucrose into 1-kestose as described in Examples 8 and 9.

After 3 hours of reaction the permeate recirculation valve to the bioreactor was closed, and the valve to the FOS collector tank previously kept closed, was opened. The valve corresponding to the retentate stream was regulated to achieve 30 mL/min of permeate flow.

Figure 6:
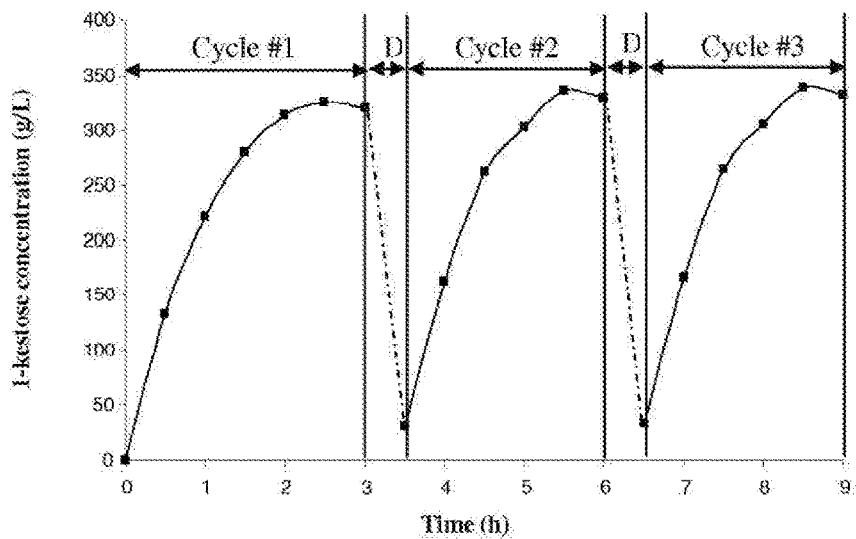
FIG. 6. Time course of 1-kestose synthesis by the enzyme 1-SSTrec in a membrane bioreactor during 3 consecutive cycles of semicontinuous operation. Reaction conditions: 1-SSTrec 9000 U/L, sucrose 600 g/L in 0.1 M sodium acetate buffer (pH 5.5); temperature 40° C., stirring speed 250 rpm. Operation sequence: Cycle no. 1, continuous synthesis reaction for 3 h and discharge (D) for 30 min. Cycles no. 2-3, continuous synthesis reaction for 2.5 h and discharge (D) for 30 min.
Figure 7:
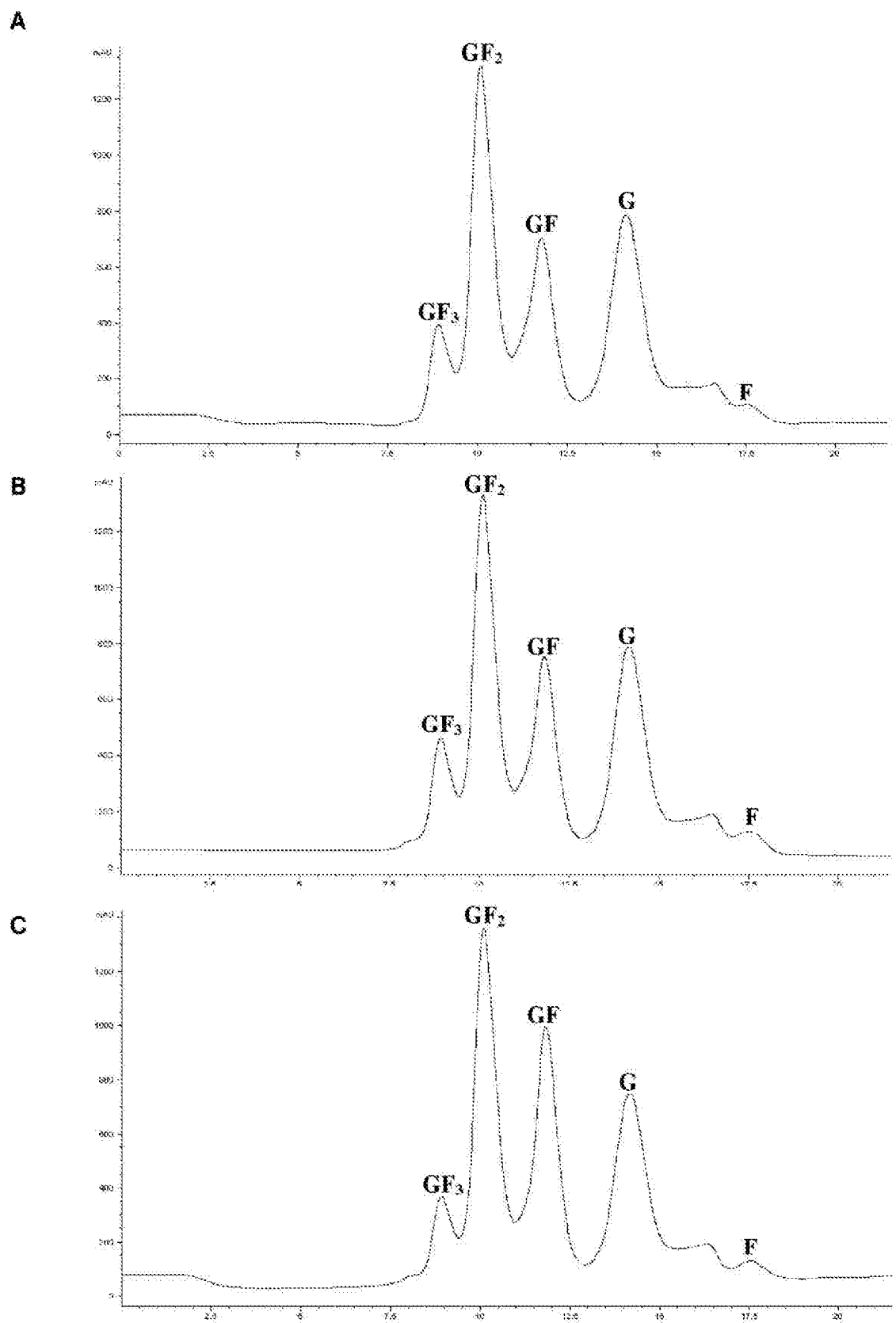
FIG. 7. HPLC chromatograms showing the product profile in samples retrieved after each consecutive cycle of FOS synthesis in a membrane bioreactor with semicontinuous operation. A, Cycle No. 1, B, Cycle No. 2. and C, Cycle No. 3. Legend: Nystose ($GF_3$), Kestose ($GF_2$), Sucrose (GF), Glucose (G), Fructose (F).

After 30 minutes, the 90% of the total reaction volume was discharged and so, the permeate outlet valve to the collection tank was closed. Then the returned back valve to the bioreactor was opened and the retained valve was regulated, so that the returning permeate flow to the bioreactor was established to 5 mL/min. At this point the bioreactor was charged with 900 mL of sucrose 600 g/L, in 0.1 M acetate buffer, pH 5.5. Also a 180 U of 1-SSTrec were added, to keep the same reaction time and the same conversion ratio of 1-kestose, thus beginning the second synthesis cycle. After 2 hours and 30 minutes of reaction the discharge of the reaction products proceeded as performed in the first cycle. After complete discharge of the 90% of the reaction volume corresponding to the second cycle, the bioreactor was loaded again in the same way as was done in the second cycle. These reaction-discharge steps are repeated sequentially up to complete 10 operation cycles and then the BRM cleaning step is carried out. FIG. 6 shows the behaviour during the first 3 cycles, and FIG. 7 shows the product profile at the end of each sequential cycle.

The use of a BRM sequentially operated has similar productivity to that of a stirred tank bioreactor with the same capacity, but consuming 8 times less enzyme by amount of produced 1-kestose.

Similar 1-kestose concentrations are obtained for other BRM operating conditions semi-continuously operated. Among operation conditions that could be varied without affecting the product profile are the ratio enzyme-substrate (2-40 U/g of sucrose), sucrose concentration 400-800 g/L, temperature (30-50° C.), pH (5.0-6.5), assuming always that the download time is between 10 and 20% of the time in which the maximum production of 1-kestose is reached.

Download times over this range favour nystose synthesis and fructose production from 1-kestose. Prior to this invention there existed no reports in the literature to describe the production of 1-kestose in a BRM.

The invention claimed is:

1. A method for the production of 1-kestose on an industrial scale characterized by the conversion of sucrose into 1-kestose in a bioreactor with the use of a recombinant fructosyltransferase (FTF) from *Festuca arundinacea* expressed constitutively in a non-saccharolytic yeast,
   wherein the yeast contains at least six copies of the gene encoding a FTF,
   wherein expression of the genes is under transcriptional control by a yeast constitutive promoter,
   wherein the FTF is a sucrose:sucrose 1-fructosyltransferase (1-SST),
   wherein the initial sucrose concentration in the bioreactor is in a range between 500 and 800 g/L.

2. The method of claim 1 wherein the non-saccharolytic yeast is a *Pichia pastoris* strain.

3. The method of claim 2 wherein the FTF is recovered from the supernatant and/or the cell sediment of the *Pichia pastoris* culture.

4. The method of claim 1 wherein the sucrose concentration is above 600 g/L.

5. The method of claim 1 wherein the FTF is produced by the recombinant yeast grown in a fermentor with discontinuous, continuous or fed-batch operation.

6. The method of claim 5 wherein the carbon source used for the yeast growth is a compound selected from glycerol, glucose and sucrose of any degree of purity.

7. The method of claim 1 wherein the sucrose conversion into 1-kestose is performed by free or immobilized 1-SST.

8. The method of claim 1 wherein the conversion of sucrose into 1-kestose is performed in a bioreactor of stirred tank, fixed bed or membrane type.

9. The method of claim 8 wherein the membrane bioreactor is operated in a continuous or semicontinuous mode.

* * * * *